US006411406B1

(12) United States Patent
Kreuzer (10) Patent No.: US 6,411,406 B1
(45) Date of Patent: Jun. 25, 2002

(54) HOLOGRAPHIC MICROSCOPE AND METHOD OF HOLOGRAM RECONSTRUCTION

(75) Inventor: H. Juergen Kreuzer, Portuguese Cove (CA)

(73) Assignee: Dalhousie University, Halifax (CA)

( * ) Notice: Subject to any disclaimer, the term of this patent is extended or adjusted under 35 U.S.C. 154(b) by 0 days.

(21) Appl. No.: 09/802,906

(22) Filed: Mar. 12, 2001

(51) Int. Cl.[7] .......................... G02B 21/00; G03H 1/10; G03H 1/16; G03H 1/22; G01N 23/201
(52) U.S. Cl. ..................... 359/10; 359/1; 359/9; 359/29; 359/32; 378/36; 378/87
(58) Field of Search ..................... 359/1, 9, 10, 29, 359/32, 35; 378/36, 87; 382/279, 280

(56) References Cited

U.S. PATENT DOCUMENTS

| | | | | |
|---|---|---|---|---|
| 4,536,883 A | * | 8/1985 | Chapline, Jr. ............... | 378/36 |
| 4,955,974 A | * | 9/1990 | Rhodes et al. ............... | 359/10 |
| 5,095,207 A | | 3/1992 | Tong ........................... | 250/306 |
| 5,227,630 A | | 7/1993 | Saldin et al. ................ | 250/307 |
| 5,432,347 A | | 7/1995 | Coene ......................... | 250/307 |
| 5,974,179 A | * | 10/1999 | Kitayoshi .................... | 382/210 |
| 6,130,957 A | * | 10/2000 | Horikoshi et al. ........... | 382/107 |

OTHER PUBLICATIONS

Denis Gabor, 'A New Microscopic Principle', Nature (London) vol. 161, pp. 777–778, May 1948.
Barton, 'Photoelectron Holography', Physical Review Letters, vol. 61, No. 12, pp. 1356–1359, Sep. 1988.
Kreuzer, Nakamura, Wierzbicki, Fink and Schmid 'Theory of the point source electron microscope', Ultramicroscopy 45, 381–403, 1992.
Kreuzer and Pawlitzek, A software package for the simulation and reconstruction of LEEPS images and other holograms, version 1.2, copyright 1993–1998.
Kreuzer H.J., "Low energy Electron Point Source Microscopy", MICRON vol. 26, No. 6, 503–509, 1995.
Schmid, Fink and Kreuzer "In–line holography using low–energy electrons and photons: applications for manipulation on a nanometer scale", J. Vac. Sci. Technol. B 13,2428–2431, 1995.
Kreuzer, Pawlitzek "Fast Implementation of In–line Holography for High Resolution Shape Measurement", Proceedings of the International Symposium on Laser applications in Precision Measurement, Akademie Verlag, Berlin 1996.
Golzhauser, Volkel, Jager, Zharnikov, Kreuzer and Grunze "Holograhic imaging of macromolecules", J. Vac. Sci. Technol. A 16(5), 3025–3028, Sep./Oct. 1998.
Kreuzer, Pomerleau, Blagrave, Jericho "Digital in–line holography with numerical reconstruction", SPIE 3744, 65–75, 1999.
E. Cuche et al., 'Simultaneous amplitude–contrast and quantative phase–constrast microscopy by numerical reconstruction of Fresnel off–axis holograms', Applied Optics, vol. 38 No. 34, pp. 6994–7001, Dec. 1999.
Golzhauser, Volkel, Grunze and Kreuzer "Optimization of the low energy electron point source microscope: imaging of macromolecules", Micron, to be published Jun. 2001.

* cited by examiner

Primary Examiner—Jon Henry (57) ABSTRACT

A holographic microscope is described along with a method for numerically reconstructing a holographic image. The method uses a coordinate transformation of the Kirchhoff-Helmholtz equation to remove the non-linear component from the phase factor. The intensity distribution in the transformed coordinate system is then interpolated on an equidistant point grid and Fast-Fourier-Transforms are used to compute the result.

25 Claims, 3 Drawing Sheets

HOLOGRAPHIC MICROSCOPE AND METHOD OF HOLOGRAM RECONSTRUCTION

FIELD OF THE INVENTION

This invention relates generally to holographic microscopy and more particularly to the numerical reconstruction of holograms.

BACKGROUND OF THE INVENTION

Conventional optical, confocal or electron microscopes have certain limitations. High resolution conventional microscopes are costly and the resolution of such microscopes is limited by the physical imperfections inherent in lenses. Conventional optical and electron microscopes take only two dimensional images. Confocal microscopes allow three dimensional imaging but only in a horizontal plane and only the auto-florescent part of a sample can be seen. If staining is used to display other parts of the sample, the staining process kills most biological specimens. Finally, the focusing time required by conventional microscopes limits how rapidly successive images of a specimen may be taken.

Holography offers solutions to some of the inherent problems with conventional microscopy. Holographic microscopy using spherical wave fronts was first proposed by Denis Gabor in 1948. He sought to overcome the limitations inherent in the use of lenses. He introduced the concept of recording not only the intensity of the wave scattered by the sample being measured but also the wave's phase. This phase information is used in a reconstruction process to reveal the three-dimensional shape of the sample being measured.

Whereas the limitation in optical microscopy is the quality of the lenses, the limitation in holographic microscopy has been the reconstruction process. Reconstruction can be either physical or numerical.

The method of reconstruction first suggested by Gabor was physical reconstruction of an in-line hologram. In in-line holography, the sample to be measured is situated close to a point source of radiation. A small fraction of the waves impinging on the sample are scattered by the sample. A hologram then results from the interference of the scattered wave and the unscattered reference wave coming directly from the source. This hologram is registered as a series of interference fringes on a photographic film in line with the point source and the sample. The reconstruction of the scattered wavefront, i.e. the "image" of the sample, is then obtained by illuminating the hologram with a duplicate of the reference wave source.

There are problems with the physical method of reconstruction for in-line holography. In particular, the reconstructed image of the sample is dominated by the much brighter, out of focus, image of the point source, and is also blurred by a "ghost" twin image. To overcome the problems of in-line holography various schemes of off-line holography have been developed. However, these methods introduce the use of lenses thereby reintroducing some of the problems sought to be overcome by holographic microscopy in the first place.

Another reconstruction method, which has been suggested to overcome the problems of in-line physical reconstruction, is numerical reconstruction. Numerical reconstruction methods commonly employ the Kirchhoff-Helmholtz reconstruction formula in various formulations. Because a phase factor in the Kirchhoff-Helmholtz formula is highly nonlinear in the spatial domain, in past applications various approximation schemes have been suggested, such as an on-axis Fraunhofer-type approximation and a range of weighting functions, to ultimately allow the use of multiple Fast-Fourier-Transforms (FFTs) for efficient high-speed reconstruction. A recent paper employing such approximations is E. Cuche et al., *Applied Optics,* 38 (1999) 6994–7001.

Most numerical reconstruction methods are unsatisfactory because the approximations used in the reconstruction methodology result in poor image quality. On the other hand, a full implementation of the Kirchhoff-Helmholtz reconstruction formula for high-resolution images requires inordinately long computation time so that any real-time implementation is out of the question. This non-real time numerical reconstruction limits the obtaining of images to post processing and does not allow for the adjustment of the measurement in response to the initial images.

SUMMARY OF THE INVENTION

The invention may be summarized according to a first broad aspect as a method of fast and accurate numerical reconstruction of large holograms, large enough to get maximum resolution, i.e. of the order of the wavelength of the radiation used. This is achieved by a nonlinear coordinate transformation of the Kirchhoff-Helmholtz formula to remove the non-linearity from the phase factor of the formula. This is followed by an image interpolation scheme to generate an equidistant intensity distribution to which FFT methods are applied. This is essentially an exact evaluation of the Kirchhoff-Helmholtz formula.

The invention may be summarized according to a another broad aspect as a practical scheme for the realization of a digital holographic microscope, which outlines the steps necessary to obtain maximum resolution, approaching the theoretical allowed maximum, including the real-time numerical reconstruction method.

Advantageously, the reconstructed image is of a higher quality, i.e. greater resolution, than those provided by previous numerical reconstruction methods.

Also advantageously, reconstruction can be conducted in real time so that adjustments may be made while the sample is still available and in position.

Additionally, the speed of processing permits rapid successive images to be viewed, which is particularly advantageous where the sample is an active biological specimen.

Further, the use of in-line holography enables the use of a simple, inexpensive apparatus and does not require staining or other treatments of biological specimens.

Finally, reconstruction can be truly three-dimensional allowing the reconstructed sample to be viewed from any direction and the structure of the specimen to be examined.

Other aspects and features of the invention will become apparent to those of ordinary skill in the art upon review of the following description of specific embodiments of the invention in conjunction with the accompanying figures.

BRIEF DESCRIPTION OF THE DRAWINGS

Preferred embodiments of the invention will now be described with reference to the attached drawings in which.

DETAILED DESCRIPTION OF THE EMBODIMENT

Figure 1:
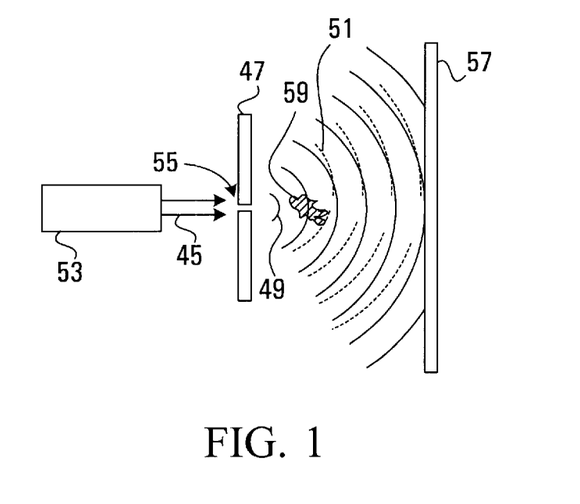
FIG. 1 is a schematic representation of a holographic microscope used to implement an embodiment of the present invention.

FIG. 1 shows an embodiment using light with a laser 53 emitting radiation 45 which illuminates a pinhole 55 in opaque material 47. The pinhole 55 acts as point source of the radiation 45. The pinhole 55 emits an approximately spherical wave 49. A small fraction of the spherical wave 49 impinges on and scatters off a sample 59 creating a scattered wave 51. The scattered wave 51 interferes with the much stronger unscattered reference spherical wave 49 producing interference fringes (a hologram) on a 2-dimensional screen or detector 57. For holography, it is necessary that the wave created by the sample be small relative to the reference wave. For electron holography, the detector 57 could be a multi-channel plate, for light it can be a CCD (Charge Coupled Device) array and for acoustic waves it can be an array of suitable mechanical/electrical receivers or microphone devices. In all such apparatuses, the hologram is recorded and transferred in digital form into a computer (not shown) for processing and numerical reconstruction of the wave front at the object. The wave front is typically reconstructed at a series of different distances from the point source 55 to locate the desired view of the sample 59. The reconstruction at various distances generates the three-dimensional structure of the object from the two-dimensional hologram on the detector 57.

Figure 2:
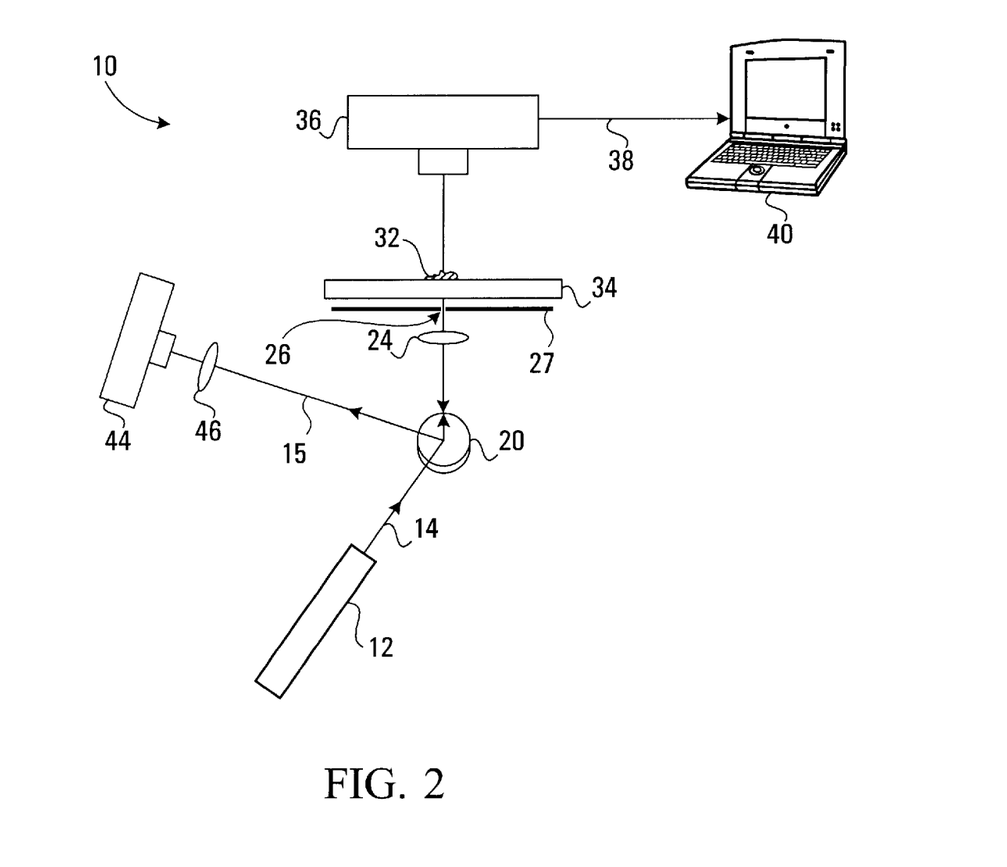
FIG. 2 is a schematic representation of a microscope which incorporates both a digital in-line holographic microscope and a conventional optical microscope.

FIG. 2 depicts a microscope 10 which has a radiation emitting device 12. In the present embodiment, the microscope 10 employs light and the radiation emitting device 12 is a laser. For other embodiments, the radiation emitting device 12 may be a device for emitting another form of radiation such as electromagnetic radiation (including x-rays, ultra-violet light, visible light, infrared light, microwaves, and radar), electron beams, acoustic waves (including ultrasonic waves) or ion beams (including Helium ions, hydrogen ions, etc.). When the microscope 10 is used as a holographic microscope, waves of radiation 14, in this case light, are emitted by the radiation emitting device 12. The waves of radiation 14 are reflected by a rotatable mirror 20 into an objective lens 24 to focus the waves of radiation 14 onto a pinhole 26 in an opaque material 27 to enhance the intensity of a point source resulting from the waves of radiation 14 being emitted through the pinhole 26. The diameter of the pinhole 26 is in the order of the wavelength of the radiation 14 emitted by the radiation emitting device 12. The end of an optical fiber could also be used as a point source and the objective lens 24 and the pinhole 26 eliminated.

A sample 32 rests on a transparent support 34, such as a glass slide or a glass whisker attached to a holder that can be moved with a micro-manipulator. The sample 32 must be very small relative to the field of the radiation emitted through the pinhole 26 and positioned relatively close to the pinhole 26, approximately in the range of $10^3$ to $10^4$ times the wavelength of the waves of radiation 14, such that the Fraunhofer condition is satisfied. The Fraunhofer condition requires $a^2 \ll d\lambda$, where "a" is the lateral dimension of the sample 32 being measured, "d" is the distance between the sample 32 and the pinhole 26, and "$\lambda$" is the wavelength of the waves of radiation 14.

A small percentage of the waves of radiation 14 impinge on the sample 32, and ultimately registers, with the unaffected waves of radiation 14, as a hologram on a detector 36 such as a CCD or other radiation measurement apparatus as described with reference to FIG. 1. The distance from the sample 32 to the detector 36 and the lateral size, pixel size and dynamics of the detector must be sufficient so that the smallest interference fringes, necessary for optimal resolution in reconstruction, are resolved. In the example shown in FIG. 2, a screen having a resolution of 1020×1532 pixels of size 9 micrometers and 8-bit dynamic is used.

The interference fringes caused by the sample 32 are recorded on the detector 36 as an intensity distribution (hologram) and transmitted by a connection 38 to a computer 40. The sample is then removed from the path of the radiation 14 and the intensity distribution (not generally referred to as a hologram since there is no sample present) is again recorded and transmitted by the connection 38 to the computer 40. The computer 40 is programmed to numerically reconstruct the image of the sample from these two measurements.

It is necessary to subtract the intensity distribution without the sample present from the intensity distribution with the sample present to eliminate any portion of the intensity distribution which is caused by imperfections in the radiation emitting device 12 or contamination in the field of the microscope. This step may be eliminated if the imperfections and the contamination can be eliminated, for example, by the use of a near perfect laser in a vacuum.

For the microscope 10 to be used as a conventional optical microscope, a lamp or ambient light (not shown) is positioned, typically in place of the detector 36, to illuminate the sample 32 with white light 15. The mirror 20 is also rotated so the white light 15 which illuminates the sample 32 reaches a CCD 44 attached to an eyepiece 46.

Figure 3:
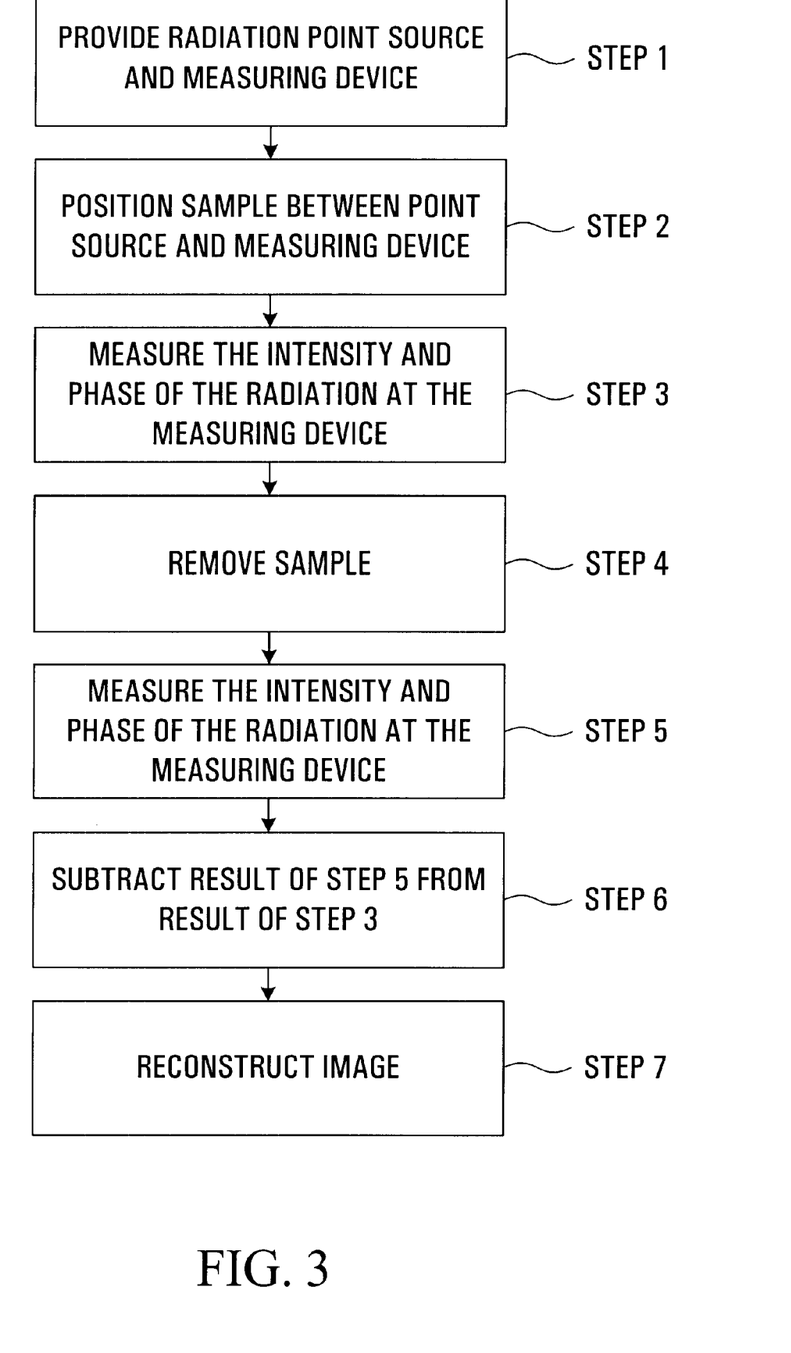
FIG. 3 is a flow chart of the operation of a microscope in accordance with the present invention.

Referring now to FIG. 3, which is a flow chart of the operation of the microscope of the present invention, the method starts with the step of providing a point source of radiation and a radiation measurement and recording apparatus (step 1). The point source and the radiation measurement apparatus are typically as described with reference to FIG. 1. The second step is to position a sample between the point source and the radiation measurement surface of the radiation measurement apparatus such that the position of the sample satisfies the Fraunhofer condition (Step 2). The third step is the measurement of the intensity of the radiation at the radiation measurement surface (Step 3). The fourth step is to remove the sample (Step 4) followed by the fifth step of again measuring the intensity of the radiation at the radiation measurement surface (Step 5). The sixth step is the subtraction of the measurement obtained without the sample from the measurement obtained with the sample (Step 6). The seventh step is the numerical reconstruction of the sample based on this differential value (Step 7).

The numerical reconstruction of the sample (Step 7) can be achieved by using the Kirchhoff-Helmholtz formula, which is:

$$K(\vec{r}) = \int_s d^2\xi I(\xi) \exp(ik\overline{\xi}\vec{r}/\xi) \qquad (1)$$

Where:
S is the two-dimensional surface of the screen. The integral extends over the surface S with coordinates $\xi=(X,Y,L)$ where X and Y are the horizontal and vertical coordinates on the screen and L is the distance from the source of the radiation (e.g. the pinhole for the optical version) to the center of the screen.

I($\xi$) is the contrast image (hologram) on the screen obtained by subtracting the image without the sample present from the image with the sample present.

k=2$\pi$/$\lambda$ is the wave number of the radiation (electromagnetic, acoustic, electron or ions)

i indicates an imaginary number $\vec{r}$(x,y,z) is a position vector at or in the vicinity of the sample with z equal to the distance from the point source to the sample, and x,y specifying the location of the reconstructed image in an x/y plane.

The function K($\vec{r}$) (the image of the sample) is different from zero and significantly structured only in the space region occupied by the sample being measured. The wave front K($\vec{r}$) is reconstructed on a number of planes at various distances from the source in the vicinity of the sample to obtain a three-dimensional image of the sample. Note that the planes do not have to be perpendicular to the optical axis between source and detector. The function K($\vec{r}$) is complex; its absolute value gives an intensity image and its phase a phase image of the sample.

The above formula as currently stated is not efficient for practical purposes to be used to derive the reconstructed image K($\vec{r}$). The following describes the numerical reconstruction process in terms of modifications and manipulations of the Kirchhoff-Helmholtz formula. It should be understood that to actually calculate the image of the sample from the recorded hologram, computations are performed on the coordinates and intensity values of the hologram, not the Kirchhoff-Helmholtz equation itself (manipulating the equation derives the related steps that must be performed on the image).

Figure 4:
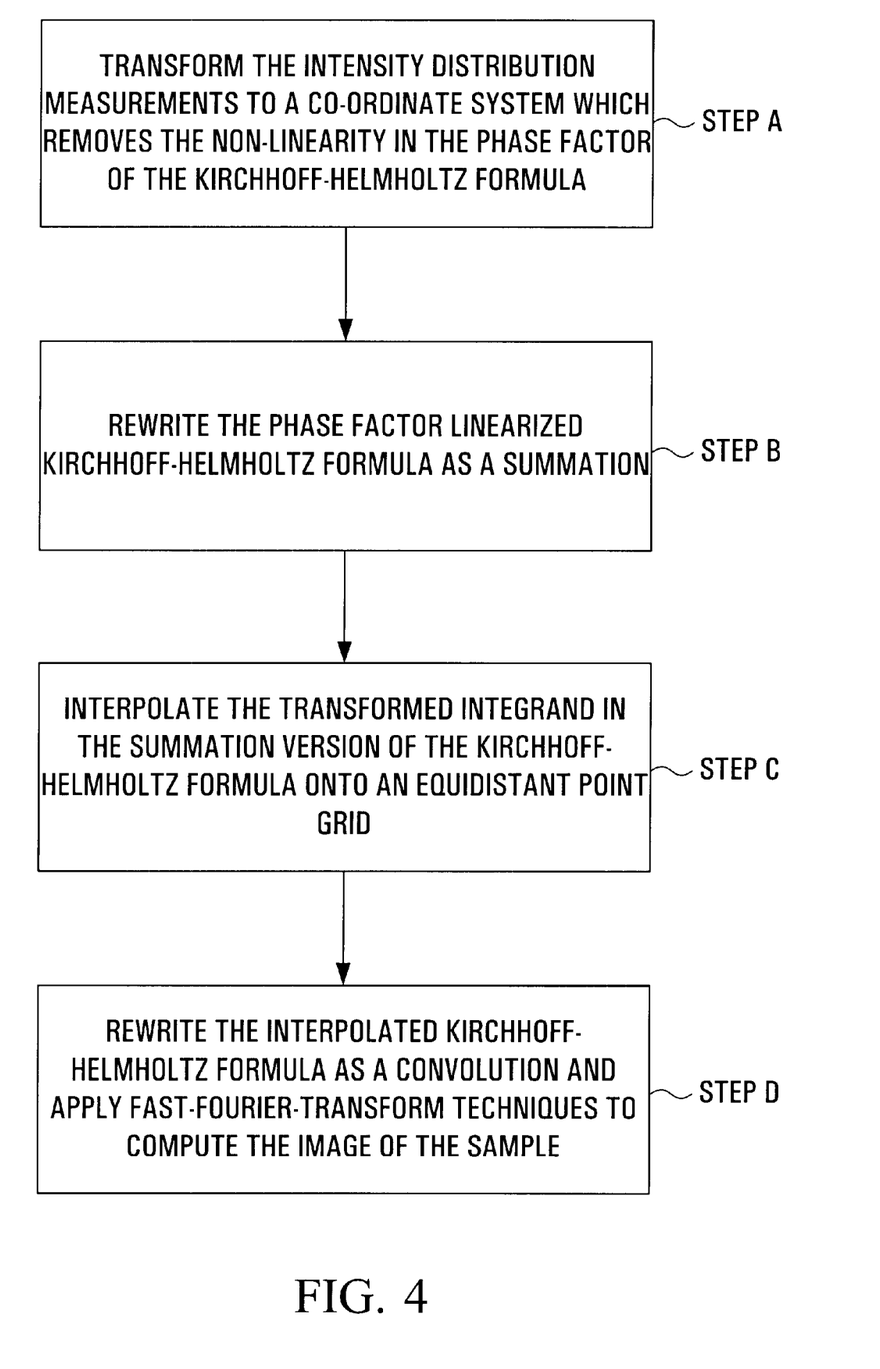
FIG. 4 is a flow chart of the method of numerical reconstruction in accordance with the present invention.

The numerical reconstruction of the present invention consists of the following steps shown in the flow chart of FIG. 4. It should be appreciated that although a specific example is given with respect to each step, other numerical implementations of the steps may be employed within the scope of the invention.

(A) Transform the intensity distribution measurements to a co-ordinate system which removes the non-linearity in the phase factor of the Kirchhoff-Helmholtz formula.

Any coordinate system which achieves this requirement may be used. For example, the new coordinate system for X', Y' and R may relate to the initial coordinate system of X, Y and L as follows:

$$X'=XL/R$$

$$Y'=YL/R$$

$$R=(L^2+X^2+Y^2)^{1/2} \qquad (2)$$

Substituting this new coordinate system into the Kirchhoff-Helmholtz formula of equation (1) defines the phase factor linearized Kirchhoff-Helmholtz formula to be:

$$K(r) = \int_{S'} dX' dY' I'(X', Y') \exp(ik(xX' + yY')/L) \qquad (3)$$

where $$I'(X', Y')=I(X(X',Y'),Y(X',Y'))(L/R')^4 \exp(ikzR'/L)$$

Note that the position dependent phase factor $\xi$ in the denominator of exp(ik$\vec{\xi} \cdot \vec{r}$/$\xi$) in the original Kirchhoff-Helmholtz formula is now a constant L.

The above specified coordinate transformation is therefore applied to the coordinates of each intensity value of the hologram to move each set of x/y coordinates to a new position in the original x/y plane. Note that, if the original screen image S is rectangular, applying the X'/Y' coordinate transformation results in the transformed image S' being barrel shaped within the space bounded by S.

(B) Discretize the double integral into a double sum, i.e. rewrite the phase factor linearized Kirchhoff-Helmholtz formula as a summation.

Using the present example, this may be done as follows:

$$K_{nm} = \sum_{j,j'=0}^{N-1} I'_{jj'} \exp(2\pi i(nj + mj')/N) \qquad (4)$$

Where N is the number of pixels in one direction of the screen. It will typically be chosen to be a multiple of 2. Although the screen may be any two dimensional shape, where a quadratic screen is used, then $$x=x_n=x_0+n\delta_x$$

$$Y=Y_m=y_0+m\delta_y$$

for n,m=0,1,2, . . . , N−1. Likewise:

$$X'=X'_j=X'_0+j\Delta'_x$$

$$Y'=Y'_{j'}=Y'_0+j'\Delta'_y$$

for j,j'=0, 1, 2, . . . , N−1.

This step (B) does not directly result in any actions being performed on the hologram coordinates and intensity values. It is merely the expression of the phase factor linearized version of the Kirchhoff-Helmholtz formula in digital form necessary for computer computation.

(C) Interpolate the transformed integrand in the summation version of the Kirchhoff-Helmholtz formula onto an equidistant point grid.

Experimental holograms are usually recorded on a flat screen, perpendicular to the optical axis and digitized on an equidistant grid of pixels. However, under the coordinate transformation introduced under (A) above, the equidistant grid was transformed into a set of non-equidistant points $(X'_j, Y'_j)$. The result of the specific transformation equations, given as an example under (A), is a barrel-shaped set of coordinates. In other words, intensity values on the hologram are located at non-integer, non-equidistant positions on an x/y plane and, as a result, are not amenable to the use of Fast Fourier Transform techniques.

In order to make the intensity values amenable to Fast Fourier Transform techniques, it is necessary to overlay a new equidistant point grid on the barrel-shaped coordinates of the intensity values and determine the intensity value of the underlying barrel-shaped image at each grid point of the new equidistant point grid. This may be done using a convention b-spline interpolation algorithm, know in the art, at each new grid point to look at the underlying intensity values at the nearby underlying grid points to interpolate the actual intensity value at the new grid point.

The set of points $(X'_j, Y'_j)$ defines the surface S'. A rectangular screen S" can be constructed that circumscribes S' where the origin is located at:

$$X'_0=X_0L/(L^2+X_0^2)^{1/2}$$

$$Y'_0=Y_0L/(L^2+Y_0^2)^{1/2}$$

and the spacing of the grid points is defined by:

$$\Delta'_x = \frac{L[X_o + (N-1)\Delta_x]}{N(L^2 + [(X_o + (N-1)\Delta_x)]^2)^{1/2}} - \frac{LX_o}{N(L^2 + X_o^2)^{1/2}}$$

$$\Delta'_y = \frac{L[Y_o + (N-1)\Delta_y]}{N(L^2 + [(Y_o + (N-1)\Delta_y)]^2)^{1/2}} - \frac{LY_o}{N(L^2 + Y_o^2)^{1/2}}$$

Substituting back into the summation form of the Kirchhoff-Helmholtz formula, the result is:

$$K_{nm} = \Delta'_x \Delta'_y \exp\{ik[(x_o + n\delta_x)X'_o + (y_o + m\delta_y)Y'_o]/L\} \times \qquad (5)$$

$$\sum_{j,j'=0}^{N-1} I'_{jj'} \exp[ik(jx_o\Delta'_x + j'y_o\Delta'_y)/L]\exp[ik(nj\delta_x\Delta'_x + mj'\delta_y\Delta'_y)/L]$$

Where $I'_{jj'}$ is the image interpolated at the points X' and Y'.

This equation can be cast into a form suitable for Fast-Fourier-Transform techniques if we choose, as an example, $$\delta_x = \frac{\lambda L}{N\Delta'_x}$$

$$\delta_y = \frac{\lambda L}{N\Delta'_y}$$

Where $\lambda = 2\pi/k$ is the wavelength of the illumination radiation.

Note that a rectangular screen S" can be constructed such that it fully encompasses surface S' and therefore zero-padding is required for the perimeter of screen S". Alternatively, screen S" can be constructed to be smaller than S' and encompass only a portion of the set of points that comprise surface S'.

Although not necessary, situating the screen symmetrically about the optical axis of the radiation emitting device simplifies the calculation of all of the preceding formulae.

Other optional mathematical manipulations may be done to the original hologram to improve the resulting reconstruction. This includes gray scale adjustment to use the maximum dynamic range of the calculation variables in the reconstruction computer program; offset subtraction, i.e. subtracting the average intensity value, to correct for drift between image and background intensity; and applying a cosine or similar filter to smooth the edges of the image to lower the boundary effects.

In order to prepare our intensity distribution for subsequent Fast Fourier Transform manipulation (see step (D) below), we apply this step (C) to our transformed intensity distribution by generating a new intensity distribution on an equidistant grid which looks identical to our transformed intensity distribution. For each $X_0'/Y_0'$ coordinate of the new grid, we interpolate the intensity to use from the nearby values of the transformed intensity distribution.

(D) Rewrite the Kirchhoff-Helmholtz formula as a convolution

The result of step (C) above may be used with Fast-Fourier-Transform techniques to reconstruct the image. However, Fast-Fourier-Transforms have the advantage of speed but the disadvantage that $\delta_x$ and $\delta_y$ impose the resolution of the construction. The present step is an optional step to overcome this limitation.

This limitation can be overcome by rewriting the summation form of the Kirchhoff-Helmholtz formula into a convolution and then use the product theorem of Fourier transforms. First define:

$$nj = [n^2 + j^2 - (n-j)^2]/2 \text{ and } mj' = [m^2 + j'^2 - (m-j')^2]/2$$

Substituting these definitions into the summation form of the Kirchhoff-Helmholtz formula results in the equation:

$$K_{nm} = \Delta'_x \Delta'_y \exp\{ik[(x_o + n\delta_x)X'_o + (y_o + m\delta_y)Y'_o]/L\} \times \qquad (6)$$

$$\exp[ik(n^2\delta_x\Delta'_x + m^2\delta_y\Delta'_y)/2L] \times$$

$$\sum_{j,j'=0}^{N-1} I'_{jj'} \exp[ik(jx_o\Delta'_x + j'y_o\Delta'_y + j^2\delta_x\Delta'_x/2 + j'^2\delta_y\Delta'_y/2)/L] \times$$

$$\exp[-ik((n-j)^2\delta_x\Delta'_x + (m-j')^2\delta_y\Delta'_y)/2L]$$

Invoking the convolution theorem on the component parts of equation (6) results in the following Fourier transformed components:

$$K'_{vv'} = \sum_{j,j'=0}^{N-1} I'_{jj'} \exp[ik(jx_o\Delta'_x + j'y_o\Delta'_y + j^2\delta_x\Delta'_x/2 + j'^2\delta_y\Delta'_y/2)/L] \qquad (7)$$

$$\exp[2\pi i(vj + v'j')/N]$$

and $$R_v = \sum_{j=0}^{N-1} \exp\{-ikj^2\delta_x\Delta'_x/2L\}\exp[2\pi ivj/N]$$

and $$R_{v'} = \sum_{j'=0}^{N-1} \exp\{-ikj'^2\delta_y\Delta'_y/2L\}\exp[2\pi iv'j'/N]$$

Then, taking the inverse Fast-Fourier-Transform of the product of the component parts $K_{vv'}$, $R_v$ and $R_{v'}$, and substituting back into equation (6) yields $$K_{nm} = \Delta'_x\Delta'_y \exp\{ik[(x_o + n\delta_x)X'_o + (y_o + m\delta_y)Y'_o]/L\} \times$$

$$\times \exp\{ik[n^2\delta_x\Delta'_x + m^2\delta_y\Delta'_y]/2L\} \times$$

$$K_{nm} = \Delta'_x\Delta'_y \exp\{ik[(x_o + n\delta_x)X'_o + (y_o m\delta_y)Y'_o]/L\} \times \qquad (8)$$

$$\exp\{ik[n^2\delta_x\Delta'_x + m^2\delta_y\Delta'_y]/2L\} \times$$

$$\sum_{v,v'} K'_{vv'} R_v R_{v'} \exp\{-2\pi i(vn + v'm)/N\}$$

Equation (8), hereinafter referred to as the 'Kreuzer' Implementation of the Kirchhoff-Helmholtz transform, is used to calculate the image in planes at various distances from the detector.

It will be appreciated by those skilled in the art that other mathematical formulations of this method may be devised which appear different but which reach the same result and are contemplated by this invention.

This step, the convolution step, is used to allow control over the resolution of the reconstructed image. The convolution step may be omitted with the result that the reconstructed image may be very small.

FIG. 4 provides a flow chart of the image reconstruction Steps A to D.

Although the present example is directed to a flat rectangular CCD screen (e.g. a CCD screen having 1532×1020 pixels and being 1.38×0.92 cm in size used to record a sample in the order of one micron), it is also effective for nonsymmetrical detectors. Calculation of the values at planes tilted with respect to the optical axis is also available by this method.

In practice, the position of the sample relative to the screen is known only within a couple of millimeters. The reconstruction of the image is done at a series of distances from the screen both to accurately locate the specimen and to obtain a three dimensional view of it.

The performance of the holographic microscope can be further enhanced by taking steps to minimize the noise from the images. This can be done by, for example (1) shielding the microscope from environmental effects such as vibrations, stray radiation, air currents and thermal effects, and (2) averaging multiple measurements of the holograms.

Although presented herein as a full two-dimensional image capture mechanism (the CCD array) and numerical reconstruction method, it will be appreciated by those skilled in the art that a one dimensional implementation of the method is also possible. Such a numerical reconstruction method of interferograms has possible applications in Synthetic Aperture Radar and the seismic fields.

It will be appreciated by those skilled in the art that, although the method of the present invention has been detailed for in-line holography with spherical waves, it is not limited to such but is equally applicable to off-line holography.

In the above described embodiment, a general purpose computer is provided with software designed to implement the image reconstruction methods. More generally, any suitable processing platform, including both general purpose, application specific, with custom hardware and/or software may be used. Furthermore, another embodiment of the invention provides a computer readable medium upon which is stored instructions for a general purpose computing platform to perform any of the image reconstruction methods described herein and equivalents, generalizations thereof.

In all of the described embodiments, the inventive reconstruction methods have been applied to holographic images. More generally in another embodiment they can be applied to any intensity distribution which lends itself to reconstruction using these methods. For example, other applications in which spherical wave fronts are generated (typically from point sources) include synthetic aperture radar, underwater acoustics, seismic reconstructions and ultrasound.

The above description of embodiments should not be interpreted in any limiting manner since variations and refinements can be made without departing from the spirit of the invention. The scope of the invention is defined by the appended claims and their equivalents.

I claim:

1. A method of numerically reconstructing a holographic image comprising the steps of:
    measuring and recording the intensity distribution of a sample;
    performing a coordinate transformation of the intensity distribution to produce a transformed intensity distribution which removes a non-linearity in a phase factor of a Kirchhoff-Helmholtz formula applied to the intensity distribution producing a phase factor linearized Kirchhoff-Helmholtz formula;
    interpolating on an equidistant point grid the transformed intensity distribution to produce an interpolated intensity distribution;
    taking a Fast-Fourier-Transform of a summation form of the phase factor linearized Kirchhoff-Helmholtz formula to produce a transformed Kirchhoff-Helmholtz formula;
    calculating an image using the transformed Kirchhoff-Helmholtz formula on the interpolated intensity distribution.

2. The method of claim 1 wherein the coordinate transformation of the intensity distribution consists of calculating a new X', Y' position for each intensity distribution measurement using the formulae X'=XL/R and Y'=YL/R, where $R=(L^2+X^2+Y^2)^{1/2}$.

3. The method of claim 1 where the step of interpolating the intensity distribution on the equidistant point grid allows for a grid of points spaced at $\Delta X=\lambda L/N\Delta X$ and $\Delta Y=\lambda L/N\Delta Y$ where $\lambda$ is the wavelength of the illuminating radiation.

4. A method of numerically reconstructing a holographic image comprising the steps of:
    measuring and recording the intensity distribution with a sample present;
    measuring and recording the intensity distribution without the sample present;
    subtracting the intensity distribution without the sample present from the intensity distribution with the sample present to obtain a net intensity distribution;
    performing a coordinate transformation of the net intensity distribution to produce a transformed intensity distribution which removes a non-linearity in a phase factor of a Kirchhoff-Helmholtz formula applied to the net intensity distribution producing a phase factor linearized Kirchhoff-Helmholtz formula;
    interpolating on an equidistant point grid the transformed intensity distribution to produce an interpolated intensity distribution;
    taking a Fast-Fourier-Transform of a summation form of the phase factor linearized Kirchhoff-Helmholtz formula to produce a transformed Kirchhoff-Helmholtz formula;
    calculating an image using the transformed Kirchhoff-Helmholtz formula on the interpolated intensity distribution.

5. The method of claim 4 further comprising the step of rewriting the transformed Kirchhoff-Helmholtz formula as a convolution before calculating the value of the transformed Kirchhoff-Helmholtz formula.

6. The method of claim 4 further comprising the step of zero padding a perimeter of the net intensity distribution on the equidistant point grid.

7. The method of claim 4 further comprising the step of subtracting an average intensity value from the net intensity distribution to center the intensity distribution around zero.

8. The method of claim 4 further comprising the step of performing a gray scale adjustment on the net intensity distribution to increase a resolution of the image by maximizing the available mathematical calculation range.

9. The method of claim 4 further comprising the step of applying a filter to the net intensity distribution to smooth boundary effects.

10. The method of claim 9 wherein the filter is a cosine filter.

11. The method of claim 4 wherein the coordinate transformation of the intensity distribution consists of calculating a new X', Y' position for each intensity distribution measurement using the formulae X'=XL/R and Y'=YL/R, where $R=(L^2+X^2+Y^2)^{1/2}$.

12. The method of claim 4 where the step of interpolating the intensity distribution on the equidistant point grid allows for a grid of points spaced at $\Delta X=\lambda L/N\Delta X$ and $\Delta Y=\lambda L/N\Delta Y$ where $\lambda$ is the wavelength of the illuminating radiation.

13. A holographic microscope comprising:
    a radiation emitting point source;
    a radiation measuring and recording apparatus which measures and records the intensity of the radiation impinging on a surface of it;

a sample holder interposed between the radiation emitting point source and the radiation measuring source and being positioned significantly closer to the radiation emitting point source than to said radiation measuring and recording apparatus;

an image recording and processing means which:
  measures and records the intensity distribution with a sample present;
  measures and records the intensity distribution without the sample present;
  subtracts the intensity distribution without the sample present from the intensity distribution with the sample present to obtain a net intensity distribution;

an image reconstruction processing means which:
  performs a coordinate transformation of the net intensity distribution to produce a transformed intensity distribution which removes a non-linearity in a phase factor of a Kirchhoff-Helmholtz formula applied to the net intensity distribution producing a phase factor linearized Kirchhoff-Helmholtz formula;
  interpolates on an equidistant point grid the transformed intensity distribution to produce an interpolated intensity distribution;
  takes a Fast-Fourier-Transform of a summation form of the phase factor linearized Kirchhoff-Helmholtz formula to produce a transformed Kirchhoff-Helmholtz formula;
  calculates an image using the transformed Kirchhoff-Helmholtz formula on the interpolated intensity distribution.

14. The microscope of claim 13 wherein the radiation emitting point source is a laser.

15. The microscope of claim 13 wherein the radiation emitting device emits acoustic waves.

16. The microscope of claim 13 wherein the radiation emitting device emits electromagnetic radiation.

17. The microscope of claim 13 wherein the radiation emitting device emits electron beams.

18. The microscope of claim 13 wherein the radiation emitting device emits ion beams.

19. The microscope of claim 13 wherein the radiation emitting point source, the radiation measuring apparatus and the sample are substantially in line.

20. The microscope of claim 13 wherein the radiation measuring apparatus is a CCD screen.

21. A method of numerically reconstructing a holographic image comprising the steps of:
  measuring and recording an intensity distribution of a sample;
  performing a coordinate transformation of the intensity distribution to produce a transformed intensity distribution which removes a non-linearity in a phase factor of a Kirchhoff-Helmholtz formula;
  interpolating on an equidistant point grid the transformed intensity distribution to produce an interpolated intensity distribution;
  calculating an image of the sample using a Kreuzer implementation of the transformed Kirchhoff-Helmholtz formula on the interpolated intensity distribution.

22. The method of claim 21 where the step of interpolating the intensity distribution on the equidistant point grid allows for a grid of points spaced at $\Delta X = \lambda L/N\Delta X$ and $\Delta Y = \lambda L/N\Delta Y$ where $\lambda$ is the wavelength of the illuminating radiation.

23. The method of claim 21 wherein the coordinate transformation of the intensity distribution consists of calculating a new X', Y' position for each intensity distribution measurement using the formulae $X'=XL/R$ and $Y'=YL/R$, where $R=(L^2+X^2+Y^2)^{1/2}$.

24. A method of numerically performing a reconstruction from an intensity distribution comprising the steps of:
  performing a coordinate transformation of the intensity distribution to produce a transformed intensity distribution which removes a non-linearity in a phase factor of a Kirchhoff-Helmholtz formula applied to the intensity distribution producing a phase factor linearized Kirchhoff-Helmholtz formula;
  interpolating on an equidistant point grid the transformed intensity distribution to produce an interpolated intensity distribution;
  taking a Fast-Fourier-Transform of a summation form of the phase factor linearized Kirchhoff-Helmholtz formula to produce a transformed Kirchhoff-Helmholtz formula;
  calculating a reconstruction using the transformed Kirchhoff-Helmholtz formula on the interpolated intensity distribution.

25. A computer readable medium having instructions stored thereon for causing a processing platform to implement a reconstruction of a recorded intensity distribution, the instructions comprising:
  code means for performing a coordinate transformation of the intensity distribution to produce a transformed intensity distribution which removes a non-linearity in a phase factor of a Kirchhoff-Helmholtz formula applied to the intensity distribution producing a phase factor linearized Kirchhoff-Helmholtz formula;
  code means for interpolating on an equidistant point grid the transformed intensity distribution to produce an interpolated intensity distribution;
  code means for taking a Fast-Fourier-Transform of a summation form of the phase factor linearized Kirchhoff-Helmholtz formula to produce a transformed Kirchhoff-Helmholtz formula; and
  code means for calculating a reconstruction using the transformed Kirchhoff-Helmholtz formula on the interpolated intensity distribution.

* * * * *

UNITED STATES PATENT AND TRADEMARK OFFICE
CERTIFICATE OF CORRECTION

PATENT NO. : 6,411,406 B1
DATED : June 25, 2002
INVENTOR(S) : H. Juergen Kreuzer It is certified that error appears in the above-identified patent and that said Letters Patent is hereby corrected as shown below:

<u>Title page,</u>
Item [56], References Cited, insert -- FOREIGN PATENT DOCUMENTS WO0020929 --.

Signed and Sealed this

First Day of April, 2003

JAMES E. ROGAN
*Director of the United States Patent and Trademark Office*